(12) United States Patent
Wand et al.

(10) Patent No.: US 10,555,770 B2
(45) Date of Patent: Feb. 11, 2020

(54) ELECTROSURGICAL TUBULAR SHAFT, SURGICAL INSTRUMENT GRIP AND ELECTROSURGICAL TUBULAR SHAFT INSTRUMENT

(71) Applicant: Aesculap AG, Tuttlingen (DE)

(72) Inventors: Matthias Wand, Tuttlingen (DE); Dieter Weisshaupt, Immendingen (DE); Markus Nesper, Tuttlingen (DE)

(73) Assignee: Aesculap AG, Tuttlingen (DE)

( * ) Notice: Subject to any disclaimer, the term of this patent is extended or adjusted under 35 U.S.C. 154(b) by 767 days.

(21) Appl. No.: 15/137,263

(22) Filed: Apr. 25, 2016

(65) Prior Publication Data

US 2016/0235476 A1 Aug. 18, 2016

Related U.S. Application Data

(63) Continuation of application No. PCT/EP2014/072044, filed on Oct. 14, 2014.

(30) Foreign Application Priority Data

Oct. 29, 2013 (DE) .......................... 10 2013 111 912

(51) Int. Cl.
*A61B 18/14* (2006.01)
*A61B 18/00* (2006.01)
(Continued)

(52) U.S. Cl.
CPC .......... *A61B 18/1445* (2013.01); *A61B 18/14* (2013.01); *A61B 2017/0046* (2013.01);
(Continued)

(58) Field of Classification Search
CPC A61B 2018/00172; A61B 2018/00178; A61B 2018/0091; A61B 18/14;
(Continued)

(56) References Cited

U.S. PATENT DOCUMENTS 4,657,016 A * 4/1987 Garito ................ A61B 17/3213
439/784
5,275,607 A 1/1994 Lo et al.
(Continued)

FOREIGN PATENT DOCUMENTS

DE 9409979 11/1994
DE 4421585 7/1995
(Continued)

OTHER PUBLICATIONS

International Search Report for corresponding application No. PCT/EP2014/072044 dated Jan. 12, 2014.

*Primary Examiner* — Daniel W Fowler
*Assistant Examiner* — Bradford C. Blaise
(74) *Attorney, Agent, or Firm* — Lipsitz & McAllister, LLC (57) ABSTRACT

An electrosurgical tubular shaft for use with a surgical instrument grip for formation of an electrosurgical tubular shaft instrument is provided. The tubular shaft comprises a tube, an electrosurgical tool arranged at the distal end on the tubular shaft, at least one electric connection line electrically connected to the tool and extending in the tube, and at least one coupling element arranged at the proximal end on the tubular shaft for interacting with at least one corresponding coupling element of the instrument grip for releasably coupling the instrument grip to the tubular shaft. The tube comprises an outlet opening which is arranged distally of the at least one coupling element and through which the at least one connection line issues from the tube. The tubular shaft comprises an electric connection element for an electric energy supply. A surgical instrument grip and an electrosurgical tubular shaft instrument are also provided.

15 Claims, 8 Drawing Sheets

(51) Int. Cl.
  *A61B 17/00* (2006.01)
  *A61B 90/00* (2016.01)
(52) U.S. Cl.
  CPC .............. *A61B 2018/00077* (2013.01); *A61B 2018/0091* (2013.01); *A61B 2018/00172* (2013.01); *A61B 2018/00178* (2013.01); *A61B 2018/00589* (2013.01); *A61B 2090/0813* (2016.02); *A61B 2560/04* (2013.01)

(58) Field of Classification Search
  CPC ............ A61B 18/1442; A61B 18/1445; A61B 18/1447; A61B 2018/145; A61B 2018/1452; A61B 2018/1455; A61B 2018/1457; A61B 2560/04; A61B 2560/0406; A61B 2560/0418; A61B 90/08; A61B 2090/0813; A61B 90/50
  See application file for complete search history.

(56) References Cited

U.S. PATENT DOCUMENTS

| | | | |
|---|---|---|---|
| 5,735,873 | A | 4/1998 | MacLean |
| 5,810,879 | A | 9/1998 | de Guillebon |
| 5,951,574 | A | 9/1999 | Stefanchik et al. |
| 6,004,320 | A | 12/1999 | Casscells et al. |
| 6,334,861 | B1 | 1/2002 | Chandler et al. |
| 8,100,907 | B2 | 1/2012 | Aue |
| 8,876,805 | B2 | 11/2014 | Kaercher et al. |
| 2002/0026202 | A1 | 2/2002 | Honey et al. |
| 2005/0203441 | A1 | 9/2005 | Voegele |
| 2007/0225754 | A1 | 9/2007 | Measamer et al. |
| 2008/0046003 | A1 | 2/2008 | Renger et al. |
| 2008/0064929 | A1 | 3/2008 | Wiedenbein |
| 2008/0140090 | A1 | 6/2008 | Aranyi et al. |
| 2008/0188848 | A1* | 8/2008 | Deutmeyer ...... A61B 17/32002 606/40 |
| 2008/0275441 | A1 | 11/2008 | Aue |
| 2008/0294192 | A1 | 11/2008 | Stefan et al. |
| 2010/0198066 | A1* | 8/2010 | Voegele ............... A61B 8/0841 600/439 |
| 2011/0137306 | A1* | 6/2011 | Allen .................... A61B 18/14 606/41 |
| 2011/0245864 | A1 | 10/2011 | Besse et al. |
| 2013/0172859 | A1 | 7/2013 | Kaercher et al. |
| 2014/0135757 | A1 | 5/2014 | Bernard et al. |
| 2014/0142566 | A1 | 5/2014 | Bernard et al. |
| 2014/0142568 | A1 | 5/2014 | Bernard et al. |
| 2014/0155890 | A1 | 6/2014 | Bernard et al. |
| 2014/0350597 | A1 | 11/2014 | Huber et al. |

FOREIGN PATENT DOCUMENTS

| | | |
|---|---|---|
| DE | 102004025041 | 12/2005 |
| DE | 69829480 | 2/2006 |
| DE | 102006007828 | 8/2007 |
| DE | 102006052407 | 5/2008 |
| DE | 202011052176 | 5/2012 |
| DE | 102011056003 | 6/2013 |
| DE | 102012200073 | 7/2013 |
| EP | 1574167 | 9/2005 |
| JP | H07507935 | 9/1995 |
| JP | 2001515751 | 9/2001 |
| JP | 2005261945 | 9/2005 |
| JP | 2008119448 | 5/2008 |
| WO | 9305718 | 4/1993 |
| WO | 95/20921 | 8/1995 |
| WO | 2009/046490 | 4/2009 |
| WO | 2013/000465 | 1/2013 |

* cited by examiner

FIG.11

ELECTROSURGICAL TUBULAR SHAFT, SURGICAL INSTRUMENT GRIP AND ELECTROSURGICAL TUBULAR SHAFT INSTRUMENT

CROSS-REFERENCE TO RELATED APPLICATIONS

This application is a continuation patent application of international application number PCT/EP2014/072044, filed on Oct. 14, 2014, and claims the benefit of German application number 10 2013 111 912.3, filed Oct. 29, 2013, which are incorporated herein by reference in their entirety and for all purposes.

FIELD OF THE INVENTION

The present invention relates to an electrosurgical tubular shaft for use with a surgical instrument grip for formation of an electrosurgical tubular shaft instrument, the tubular shaft comprising a tube, an electrosurgical tool arranged at the distal end on the tubular shaft, at least one electric connection line electrically connected to the tool and extending in the tube, and at least one coupling element arranged at the proximal end on the tubular shaft for interacting with at least one corresponding coupling element of the instrument grip for releasably coupling the instrument grip to the tubular shaft.

The invention also relates to a surgical instrument grip for use with an electrosurgical tubular shaft for formation of an electrosurgical tubular shaft instrument, comprising at least one coupling element for interacting with at least one corresponding coupling element of the tubular shaft for releasably coupling the tubular shaft to the instrument grip.

The invention further relates to an electrosurgical tubular shaft instrument, comprising a surgical instrument grip and an electrosurgical tubular shaft which is releasably connectable to the instrument grip.

Herein, "proximal" and "distal" are to be construed as relating to use of the tubular shaft, the instrument grip and the tubular shaft instrument for their intended purpose, with the tubular shaft interacting at the proximal end and the instrument grip at the distal end. The user acts from the proximal end on the instrument grip and operates with the tool arranged at the distal end on the tubular shaft.

BACKGROUND OF THE INVENTION

A tubular shaft and an instrument grip of the aforementioned kind can be releasably connected to each other by the respective coupling elements forming a coupling device, in order to form an aforementioned electrosurgical tubular shaft instrument. For this purpose, the instrument grip usually comprises a sleeve-shaped receptacle into which the tubular shaft is partially insertable and in which it is releasably lockable. By means of at least one grip element of the instrument grip, it is usually possible to act on a pulling and/or pushing force transmission element guided in the tube, which is coupled at the distal end to the tool, so that the tool can be actuated with the at least one grip element.

The tool of the tubular shaft is electrically connected to at least one electric connection line, so that the tool can be supplied with electrosurgical energy. For electrical safety reasons, the at least one connection line extends in the tube, and it can thereby also be kept away from the operating site, which improves the handling of the tubular shaft. In the known tubular shaft instruments, the at least one electric connection line as well as the at least one coupling element are introduced into the instrument grip in which the electric connection line is contacted by electric contact members. For this purpose, the instrument grip, for its part, is connected by a further electric connection line to an electric energy supply. These tubular shafts, instrument grips and, consequently, tubular shaft instruments have a relatively complicated construction as only relatively little constructional space is available for mechanical connection of the tubular shaft to the instrument grip and electric contacting of the at least one connection line in the instrument grip. With exchangeable tubular shaft systems in which a reusable instrument grip is used with one-way tubular shafts, such mechanical coupling and electric contacting in the instrument grip makes cleaning, in particular, sterilization, thereof, after operational use, difficult.

An object underlying the present invention is to provide a generic tubular shaft, a generic instrument grip and a generic tubular shaft instrument, so that the tubular shaft instrument formed by the tubular shaft and the instrument grip has a constructionally simpler design.

SUMMARY OF THE INVENTION

In a first aspect of the invention, an electrosurgical tubular shaft for use with a surgical instrument grip for formation of an electrosurgical tubular shaft instrument is provided, the tubular shaft comprising a tube, an electrosurgical tool arranged at the distal end on the tubular shaft, at least one electric connection line electrically connected to the tool and extending in the tube, and at least one coupling element arranged at the proximal end on the tubular shaft for interacting with at least one corresponding coupling element of the instrument grip for releasably coupling the instrument grip to the tubular shaft. The tube comprises an outlet opening which is arranged distally of the at least one coupling element and through which the at least one connection line issues from the tube, and in that the tubular shaft comprises an electric connection element for an electric energy supply, which is arranged at the proximal end on the at least one connection line.

In a second aspect of the invention, a surgical instrument grip for use with an electrosurgical tubular shaft in accordance with the first aspect for formation of an electrosurgical tubular shaft instrument is provided, the instrument grip comprising at least one coupling element for interacting with at least one corresponding coupling element of the tubular shaft for releasably coupling the tubular shaft to the instrument grip, and at least one connecting element for releasably fixing the at least one connection line of the tubular shaft to the instrument grip.

In a third aspect of the invention, an electrosurgical tubular shaft instrument, comprises a surgical instrument grip and an electrosurgical tubular shaft in accordance with the first aspect are provided. The tubular shaft is connectable to the instrument grip, and the tubular shaft comprises at least one connecting element for releasably fixing the at least one connection line to the instrument grip, which interacts with the at least one correspondingly constructed connecting element of the instrument grip.

BRIEF DESCRIPTION OF THE DRAWINGS

The foregoing summary and the following description may be better understood in conjunction with the drawing figures, of which.

DETAILED DESCRIPTION

Although the invention is illustrated and described herein with reference to specific embodiments, the invention is not intended to be limited to the details shown. Rather, various modifications may be made in the details within the scope and range of equivalents of the claims and without departing from the invention.

The present invention relates to an electrosurgical tubular shaft for use with a surgical instrument grip for formation of an electrosurgical tubular shaft instrument, the tubular shaft comprising a tube, an electrosurgical tool arranged at the distal end on the tubular shaft, at least one electric connection line electrically connected to the tool and extending in the tube, and at least one coupling element arranged at the proximal end on the tubular shaft for interacting with at least one corresponding coupling element of the instrument grip for releasably coupling the instrument grip to the tubular shaft. The tube comprises an outlet opening which is arranged distally of the at least one coupling element and through which the at least one connection line issues from the tube, and in that the tubular shaft comprises an electric connection element for an electric energy supply, which is arranged at the proximal end on the at least one connection line.

With the tubular shaft in accordance with the invention, the at least one electric connection line extends from the tool in the distal-proximal direction in the tube. Through the outlet opening, the at least one connection line can issue from the tube at a distal spacing from the at least one coupling element. The at least one connection line, therefore, has a distal section extending in the tube and a proximal section extending outside the tube. Arranged at the proximal end on the at least one connection line is an electric connection element, which is connectable to an electric energy supply, so that the tool can be supplied with electrosurgical energy by way of the at least one connection line. Owing to the distal section of the at least one connection line extending in the tube, the electrical safety of the tubular shaft can be ensured, and the connection line is arranged far from the operating site, in order to facilitate the handling of the tubular shaft. The arrangement of the proximal section of the at least one connection line outside of the tube facilitates its electric contacting considerably. The connection line can be led outside past the instrument grip or along it and be contacted outside of the instrument grip. In particular, an instrument grip interacting with the tubular shaft in accordance with the invention does not need to have any inside electric contact members. Owing to the arrangement outside of the tube and the instrument grip, the connection element of the tubular shaft can be made sufficiently large for it to be easy to handle by a user. A filigree configuration of electric contact members as in generic tubular shafts and instrument grips can thereby be avoided. This also makes it possible for a more robust construction to be imparted to the tubular shaft and the instrument grip.

The outlet opening is expediently arranged in the proximity of the proximal end of the tube, so that the at least one connection line extends over as large a distance as possible in the tube. For example, when the tube engages the instrument grip, the outlet opening is essentially arranged immediately distally of the instrument grip.

The at least one connection line preferably issues at the side from the tube, transversely to a direction defined by the tube. This makes it possible for the tube to engage with a section arranged proximally of the outlet opening in the instrument grip, for example, for coupling with it.

In a constructionally simple configuration of the tubular shaft, the outlet opening is a through-opening which is formed in the tube and through which the at least one connection line issues from the tube.

It is advantageous for the tubular shaft to comprise a bushing, receiving the tube, for insertion into a corresponding sleeve of the instrument grip, the bushing comprising at the proximal end at least one coupling element, and for there to be formed in the bushing a through-opening through which the at least one connection line is led. The bushing makes it possible by way of the at least one coupling element for the tubular shaft to be coupled to the instrument grip, the sleeve of which may have a corresponding coupling element for this purpose. The tube can be reinforced and thereby protected by way of the bushing. The at least one connection line having issued from the tube is led through the through-opening formed in the bushing, which is expediently in alignment with the outlet opening on the tube.

The tubular shaft preferably comprises a sheath surrounding at least in sections the at least one connection line at its section which has issued from the tube. The sheath enables protection and/or guidance of the at least one connection line. For example, the sheath is configured as channel or as protective sleeve in which the at least one connection line is guided. The sheath can surround the connection line with positive locking and be fixed to it. It may be provided that the at least one connection line is not surrounded by the sheath in the area of the outlet opening so that the at least one connection line can be folded or bent for easier handling of its section which has issued from the tube. Proximally of the outlet opening, the connection line is, on the other hand, preferably surrounded by the sheath.

The sheath is preferably of elongate construction, in particular, straight-lined.

The sheath is advantageously resistant to bending, so that the at least one connection line can be protected in a better way. In this context, "resistant to bending" is to be understood as meaning, in particular, that the force required for bending the sleeve significantly exceeds the force required for bending the at least one connection line.

In a different kind of advantageous embodiment, the sheath is flexible. For example, it is a flexible hose.

A preferred embodiment of the tubular shaft in accordance with the invention is a bipolar electrosurgical tubular shaft and comprises two electric connection lines electrically connected to the tool. The tool comprises, for example, two jaw parts, each of which is electrically connected to one of the connection lines. The jaw parts can thereby be provided with different electric polarity. By supplying energy to the tubular shaft, an electric current, in particular, a high-frequency current, can flow between the jaw parts, in order to coagulate body tissue.

For example, in the last-mentioned preferred embodiment of the tubular shaft in accordance with the invention, the tool may be a forceps tool, with the two jaw parts being connected to connection lines of different polarity.

If more than one connection line is provided, it is advantageous for a common connection element to be provided, which is arranged at the proximal end on both connection lines. This allows both connection lines to be connected at the proximal end to an energy supply by a common connection element.

Further provision may be made for the two (or more) electric connection lines to be surrounded at their sections which have issued from the tube by a common sheath. For protection and/or easier handling, two (or more) connection lines may be combined by the sheath outside of the tube.

It may be provided that the tubular shaft comprises at least one contact member which is accommodated in the connection element and is electrically connected to the at least one connection line. For example, the connection element is configured as plug, which has a body enclosing the at least one contact member. For example, the at least one contact member is molded in the body and electrically connected therein to the at least one connection line. If two or more electric connection lines are provided, two or more contact members are expediently accommodated in the connection element, each electrically connected to one of the connection lines.

The at least one electric contact member can be arranged on a proximal end face of the connection element, and it can extend axially or axially parallel to a proximal-distal direction defined by the tubular shaft. The at least one contact member may be a male or female contact member.

The at least one connection line may be releasably connectable to the connection element in which the at least one contact member is accommodated. For example, the at least one connection line may be connected by way of an electric plug connection to the connection element and thereby electrically contact the at least one contact member.

It is advantageous for the tubular shaft to comprise at least one connecting element for releasably fixing the at least one connection line to the instrument grip. The section of the at least one connection line which has issued from the tube can be fixed to the instrument grip of the formed tubular shaft instrument by means of the at least one connecting element fixed or fixable to the connection line, so that the handling of the tubular shaft instrument is improved. The releasable connection of the at least one connection line to the instrument grip also allows an exchangeable tubular shaft system to be provided, with which a reusable instrument grip can be used with several tubular shafts. For each use of a tubular shaft, the at least one connection line thereof is connected to the instrument grip and, after use, released from it again, so that the tubular shaft can be removed and disposed of in a user-friendly manner.

The at least one connecting element may be a clamping element and/or a locking element; it may be fixable with positive locking and/or force locking to the instrument grip. It is also conceivable for the at least one connecting element to be fixable to the instrument grip by screwing.

The at least one connecting element can preferably be connected to and/or released from the instrument grip without a tool. The at least one connecting element preferably interacts with a correspondingly constructed connecting element of the instrument grip, so that the connecting elements form a connecting device for releasable fixing of the at least one connection line to the instrument grip.

It is expedient for the connection element to comprise or form a connecting element. This makes a constructionally simple configuration of the tubular shaft possible. In particular, it is advantageous for no further connecting element of the tubular shaft to be provided apart from the connecting element comprised or formed by the connection element.

The connecting element is preferably formed in one piece with the connection element so as to enable a constructionally simple configuration of the tubular shaft.

It proves advantageous for the at least one connecting element to comprise a projection which is insertable into a corresponding receptacle on the instrument grip, the receptacle being a connecting element of the instrument grip, which is constructed so as to correspond to the projection. Clamping and/or locking of the projection to the receptacle are, for example, possible so as to enable a connection of the connecting element to the instrument grip with force locking and/or positive locking. A screw connection of projection and receptacle is also possible.

Alternatively or additionally, it may be provided that the at least one connecting element comprises a receptacle on the connection element, into which a corresponding projection on the instrument grip is insertable.

The projection may, for example, be arranged at the distal end on the at least one connecting element, in particular, on a distal end face of the connecting element. This allows a compact construction to be imparted to the tubular shaft instrument when a connecting element constructed so as to correspond to the projection is arranged at the proximal end on the instrument grip, for example, on a proximal end face.

The projection may be configured, in particular, as rib or strip.

It is advantageous for the projection to define an axis which is aligned at an angle to a proximal-distal axis defined by the tube. The axis defined by the projection can define an insertion direction for insertion thereof into the receptacle on the instrument grip. The angle between the axis of the projection and the proximal-distal axis can, for example, ensure that the projection is not inserted axially along the proximal-distal axis into the receptacle (or parallel thereto). This allows the pulling force on the at least one connection line to be reduced when inserting the projection into the receptacle and any possible damage to the connection line to thereby be prevented.

The angle between the axes is advantageously an acute angle. It may, for example, be from approximately 70° to approximately 85°, for example, approximately 80°. A leading end of the projection when inserting the projection into the receptacle is expediently arranged more distally than an end of the projection that is last inserted into the receptacle, so that an undercut can be formed between the at least one connecting element of the tubular shaft and the corresponding connecting element on the instrument grip. The acute angle between the axes can, therefore, be construed as relating to a proximal-distal direction and an insertion direction of the projection into the receptacle on the instrument grip.

It is expedient for the at least one connecting element to comprise or form an abutment member for the instrument grip, in particular, on a distal end face. A reliable relative positioning of the at least one connecting element and the instrument grip can thereby be ensured. For example, the at least one connecting element can abut in flange-like manner by way of the abutment member on the instrument grip. The abutment member may be of planar configuration, and it can define a plane, parallel to which the aforementioned axis defined by the projection extends. The plane may be inclined relative to a proximal-distal axis. The aforementioned projection may project in the distal direction from the abutment member.

It proves expedient for the at least one connecting element to have a cylindrical or substantially cylindrical outer contour, in particular, in the circumferential direction of a proximal-distal axis defined by the tube. The at least one connecting element is, for example, of cylindrical and, in particular, disk-shaped configuration with a cylindrical outer contour, which is expediently adapted to an outer contour of the instrument grip. This allows the thus formed tubular shaft instrument to be given a more pleasing appearance and simplifies its handling.

The present invention further relates to a surgical instrument grip for use with an electrosurgical tubular shaft for formation of an electrosurgical tubular shaft instrument. The instrument grip is designed for use with a tubular shaft of the aforementioned kind and comprises at least one coupling element for interacting with at least one corresponding coupling element of the tubular shaft for releasably coupling the tubular shaft to the instrument grip. The instrument grip comprises at least one connecting element for releasably fixing the at least one connection line of the tubular shaft to the instrument grip.

The advantages achievable with use of the tubular shaft in accordance with the invention or advantageous embodiments thereof could also be achieved with the instrument grip in accordance with the invention, and so reference is to be had in this connection to the above explanations. In particular, the at least one connection line of the tubular shaft is releasably fixable to the instrument grip, which, for this purpose, comprises at least one connecting element. The at least one connecting element can interact, in particular, with the aforementioned at least one connecting element which is fixed or fixable to the section of the connection line which has issued from the tube and can form a connecting device with this connecting element. The at least one connecting element of the instrument grip can be constructed for clamping and/or locking, for positive locking and/or force locking connection. A connection of the at least one connection line to the instrument grip without a tool and/or a release of the at least one connection line from the instrument grip without a tool are also possible. It is also conceivable for the connecting elements to be screwed to each other.

The at least one connecting element is preferably arranged at the proximal end on the instrument grip, in particular, on a proximal end face of the instrument grip.

In a constructionally simple configuration, the at least one connecting element may, for example, comprise or form a receptacle into which the at least one electric connection line is insertable. For example, the electric connection line can be clamped in the receptacle.

It is advantageous for the at least one connecting element to comprise or form a receptacle into which a projection arranged on the at least one electric connection line is insertable, in particular, for fixing of the projection with force locking and/or positive locking in the receptacle.

Alternatively or additionally, the at least one connecting element can have a projection which is insertable into a correspondingly constructed receptacle of a connecting element of the tubular shaft.

The receptacle is preferably blind hole-shaped. It is then only possible for the projection to be inserted in one insertion direction into the receptacle. This facilitates the handling of the instrument grip and helps to avoid faulty connection of the at least one connection line to the instrument grip.

It is advantageous for the receptacle to define an axis which is aligned at an angle to a proximal-distal axis defined by the instrument grip. As mentioned above, the alignment of the axes at an angle to each other allows the projection not to be inserted in a purely axial direction into the receptacle. The pulling force on the at least one connection line can thereby be kept as low as possible.

The angle between the axes is preferably an acute angle and can be, for example, from approximately 70° to approximately 85°, in particular, approximately 80°. The receptacle preferably comprises an insertion opening for insertion of the projection, which is arranged more proximally than an end of the receptacle, which is located opposite the insertion opening, for example, a bottom of the blind hole. The projection can thereby be inserted from proximal to distal, so to speak, obliquely to the distal-proximal axis into the receptacle, in order to form an undercut between the projection and the receptacle and thereby enable reliable fixing of the at least one connection line to the instrument grip.

In another kind of configuration of the connecting elements, it is conceivable for the connection element to be able to be connected to the instrument grip axially along a grip axis defined by the instrument grip. The projection and the corresponding receptacle can be axially inserted into each other and, in particular, connected in a clamping and/or locking manner to each other. A screw connection of the projection in the receptacle or a bayonet-type connection is also conceivable, with the connection element being rotated or pivoted relative to the instrument grip in order to connect these to each other.

In an advantageous embodiment of the instrument grip, the connecting element comprises a projection, which is configured as Luer connector, in particular, for a Luer lock connection with the connection element of the tubular shaft. The connection element can be connected by screwing to the instrument grip, with the Luer projection on the instrument grip engaging a Luer receptacle on the connection element.

The Luer connector is preferably configured for connection of a flushing pipe, so that the instrument grip can be acted upon from the proximal end with a flushing liquid and cleaned. The connection of a flushing pipe will be discussed in greater detail hereinbelow.

It proves advantageous for the at least one connecting element to comprise or form an abutment member for a connecting element of the tubular shaft, in particular, on a proximal end face of the instrument grip. The abutment member is, for example, of planar configuration, and it can define a plane aligned at an angle relative to the proximal-distal direction. The abutment member may, for example, be constructed for flange-like abutment on the at least one connecting element of the tubular shaft. The arrangement of the at least one abutment member on a proximal end face of the instrument grip makes a compact construction of the instrument grip possible.

It is advantageous for the instrument grip to comprise a sleeve-shaped main body and a closure element connected at the proximal end to the main body for closing the main body. The tubular shaft can be inserted at least partially from the distal end into the sleeve-shaped main body and thereby couple with the instrument grip. The closure member is provided at the proximal end in order to protect the main body at the proximal end. The closure member may close the main body in a sealing or non-sealing manner. It may, in particular, be provided that an exchange of medium between the interior of the main body and the environment is possible through the closure element. For example, the closure element is plug-shaped, stopper-shaped or cap-shaped.

The closure element preferably has a through-channel in the proximal-distal direction. This allows a flushing pipe to be connected proximally to the instrument grip and a flushing liquid for cleaning the instrument grip to be introduced through the closure element into the main body.

The closure element advantageously comprises the at least one connecting element or forms it so as to enable a constructionally simple configuration of the instrument grip. For example, the connecting element comprises the aforementioned Luer projection for connecting a flushing pipe.

The at least one connecting element is preferably formed in one piece with the closure element, also in order to achieve a constructionally simple configuration.

It is expedient for the closure element to be releasably connectable to the main body. This makes it possible, for example, to exchange the closure element, if required, for another closure element which, for example, does not have or form a through-channel and/or a connecting element. It is also conceivable to have a closure element comprising or forming a through-channel and/or a connecting element separately available and to connect it to an instrument grip, so that the functions and advantages explained hereinabove can be achieved with the instrument grip.

It may be provided that the at least one connecting element has a cylindrical or substantially cylindrical outer contour, in particular, in the circumferential direction of a proximal-distal axis defined by the instrument grip. The outer contour of the connecting element of the instrument grip may, in particular, be adapted to the outer contour of a connecting element of the tubular shaft.

In an advantageous embodiment of the instrument grip in accordance with the invention, the instrument grip is an axial grip and has a sleeve-shaped main body and at least one actuatable grip element which is transferable from a spread position to a close-up position relative to the main body. The at least one grip element is, for example, mounted for pivotal movement on the main body, and, in the spread position, it can assume a non-actuation position, and, in the close-up position, an actuation position. By actuating the grip element, the tool of a tubular shaft coupled to the instrument grip can be acted upon and actuated. The at least one grip element is, for example, of half-shell-shaped or substantially half-shell-shaped configuration and can surround in sections the main body in the circumferential direction in the close-up position. In particular, two actuatable grip elements may be provided.

The present invention further relates to an electrosurgical tubular shaft instrument. A tubular shaft instrument in accordance with the invention, which accomplishes the object mentioned at the outset comprises one of the instrument grips described hereinabove and one of the tubular shafts described hereinabove, which is releasably connectable to the instrument grip, the tubular shaft comprising at least one connecting element for releasably fixing the at least one connection line to the instrument grip, which interacts with the at least one correspondingly constructed connecting element of the instrument grip.

The advantages achievable with the tubular shaft in accordance with the invention and advantageous embodiments thereof and with the instrument grip in accordance with the invention and advantageous embodiments thereof can also be achieved with use of the tubular shaft instrument in accordance with the invention. Reference is made in this connection to the above explanations.

The connecting elements form a connecting device for attachment of the at least one connection line to the instrument grip with force locking and/or positive locking, in a clamping and/or locking manner and/or without a tool. It is also conceivable to form a screw connection or a bayonet-type connection.

The instrument grip can define a proximal-distal axis which can be made to coincide with a proximal-distal axis defined by the tube of the tubular shaft when the instrument grip and the tubular shaft are coupled to each other. The direction defined by this axis will be referred to hereinbelow as axial direction.

It is expedient for the at least one connection line to be of such dimensions that with its section which has issued from the tube it is free or substantially free of axial pulling and/or pushing forces. In particular, it is thus possible to connect the at least one connection line in a strain-relieved or substantially strain-relieved manner to the instrument grip. As a result, the at least one connection line is only subjected to low strains and stresses and so damage to it can be largely avoided.

A compact construction of the tubular shaft instrument may, for example, be achieved by the section of the at least one connection line which has issued from the tube extending axially parallel from distal to proximal along the instrument grip, at least in sections.

The section which has issued from the tube extends, in particular, at least in sections, parallel to the main body of the instrument grip. It may be provided that the section or a sheath surrounding the section lies against the main body.

It is advantageous for the section of the at least one connection line which has issued from the tube to extend transversely to the axial direction alongside an actuatable grip element of the instrument grip for acting on the tool. It can thereby be ensured that the section of the at least one connection line does not interfere with actuation of the grip element. It is expediently provided that the grip element does not contact the section of the at least one connection line when transferring from a non-actuation position to an actuation position.

As mentioned above, it may be provided that the instrument grip comprises two actuatable grip elements for acting on the tool. Here provision is expediently made for the section of the at least one connection line which has issued from the tube to extend between the grip elements, in relation to a direction transverse to the axial direction. A compact construction of the tubular shaft instrument can thereby be achieved.

It has also been mentioned hereinabove that the outer contours of the at least one connecting element of the tubular shaft and of the at least one connecting element of the instrument grip may be adapted to each other. In the state in which they are connected to each other, the connecting elements may have a common outer contour, which is, so to speak, continuous. This imparts a more pleasing appearance to the tubular shaft instrument and facilitates its handling.

For example, it may be provided that the connecting elements each have, in particular, in the circumferential direction of a proximal-distal axis defined by the instrument grip, a cylindrical or substantially cylindrical outer contour of the same diameter.

Figure 1:
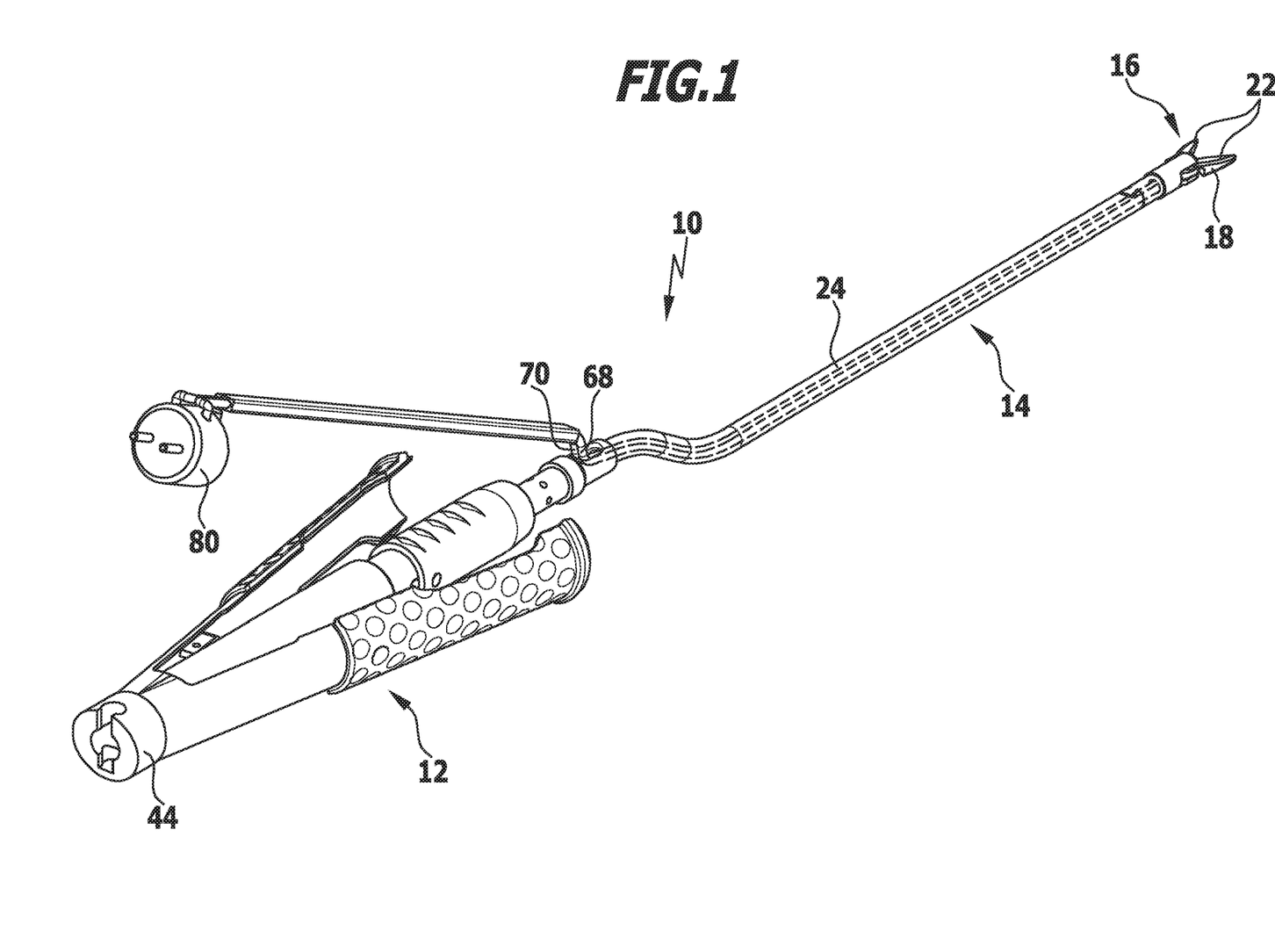
FIG. 1 shows a perspective view of a preferred embodiment of a tubular shaft instrument in accordance with the invention, comprising a preferred embodiment of a tubular shaft in accordance with the invention and a preferred embodiment of an instrument grip in accordance with the invention, wherein the tubular shaft and the instrument grip are shown in a state in which they are not yet connected to each other.
Figure 2:
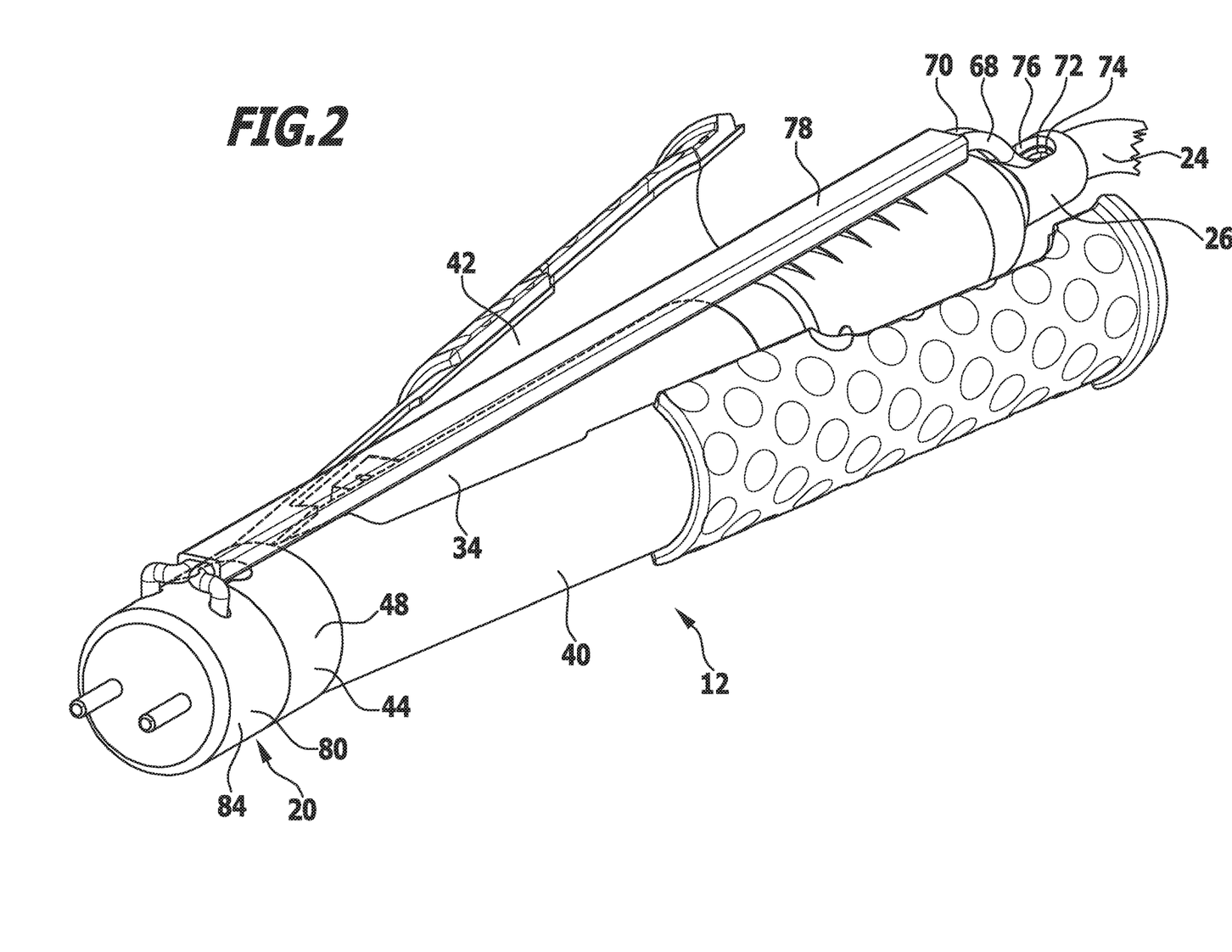
FIG. 2 shows an enlarged representation of a proximal section of the tubular shaft instrument from FIG. 1, wherein the tubular shaft and the instrument grip are connected to each other.
Figure 7:
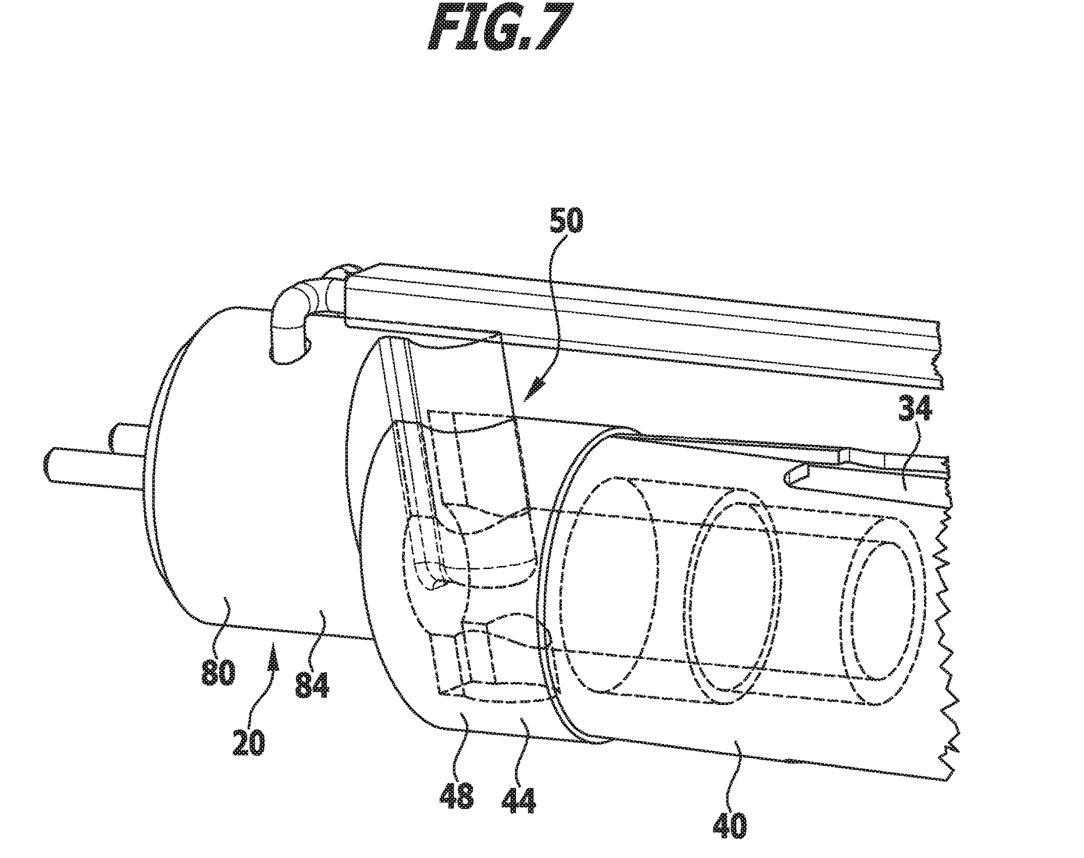
FIG. 7 shows a partial representation of a proximal end area of the tubular shaft instrument from FIG. 1, wherein the connection element from FIG. 3 is connected to the closure element from FIG. 5.
Figure 8:
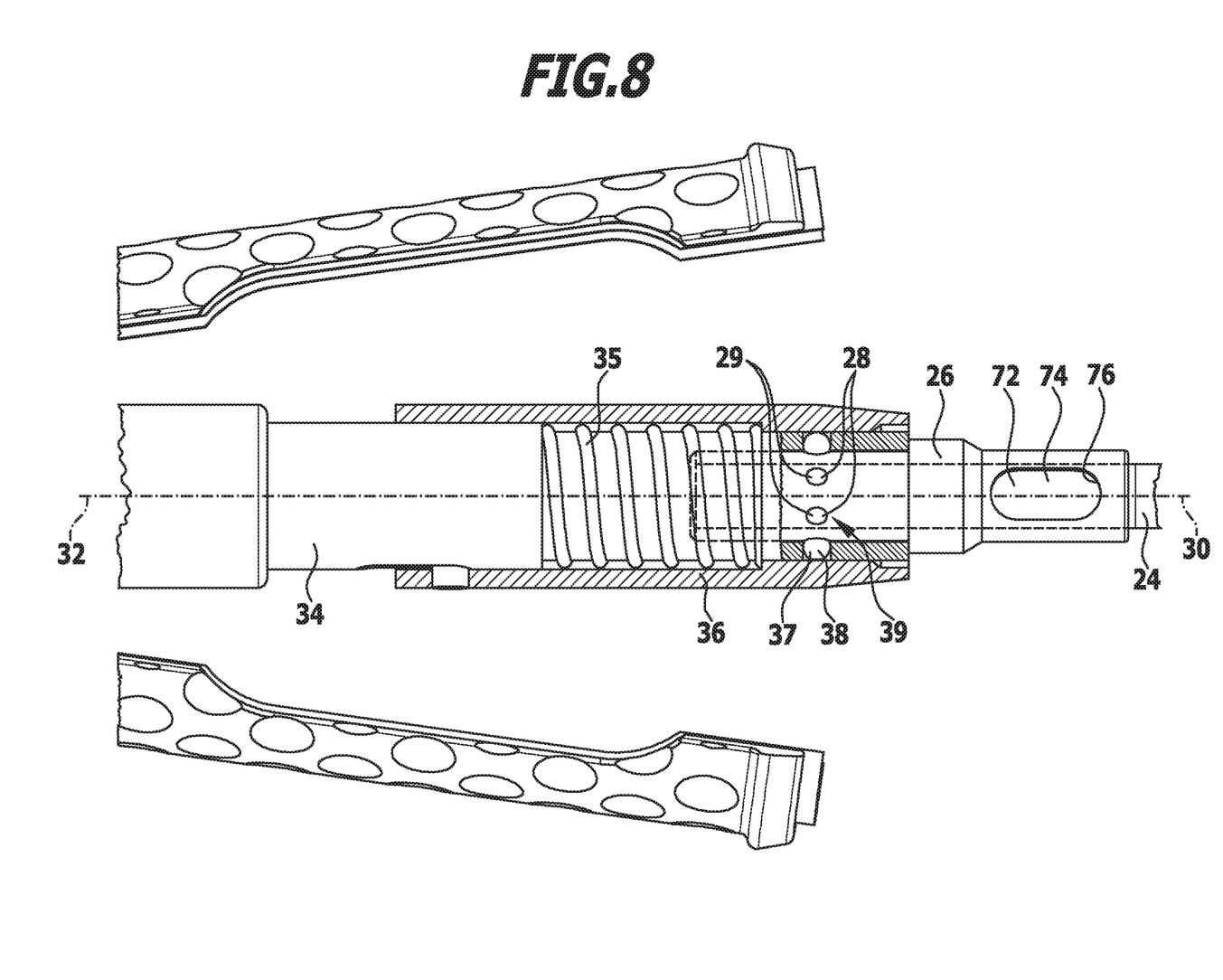
FIG. 8 shows a partial representation of a distal end area of the instrument grip and the proximal end area of the tubular shaft from FIG. 1, partly in section.

FIG. 1 shows in perspective representation a preferred embodiment of an electrosurgical tubular shaft instrument in accordance with the invention, denoted in its entirety by reference numeral 10. The tubular shaft instrument 10 comprises a preferred embodiment of a surgical instrument grip in accordance with the invention, denoted by reference numeral 12, and a preferred embodiment of an electrosurgical tubular shaft in accordance with the invention, denoted by reference numeral 14. The instrument grip 12 and the tubular shaft 14 are releasably connectable to each other and are shown (partially) in FIGS. 1 and 7 while they are being connected to each other, whereas the instrument grip 12 and the tubular shaft 14 are shown in FIGS. 2 and 8 (partially in each case) in the state in which they are connected to each other.

Herein, position and orientation indications such as "proximal", "distal", "proximal-distal" and the like are to be construed as relating to use of the tubular shaft instrument 10 for its intended purpose, during which the instrument grip 12 and the tubular shaft 14 are connected to each other. During use for its intended purpose, the user acts from the proximal direction on the tubular shaft instrument 10 and operates with a tool 18 arranged at the distal end 16 of the tubular shaft instrument 10. The proximal end of the tubular shaft instrument 10 is denoted by reference numeral 20.

The tubular shaft 14 is a bipolar electrosurgical tubular shaft and comprises at the distal end the aforementioned tool 18, which is configured as a forceps tool with two jaw parts 22 movable and, in particular, pivotable relative to each other. The jaw parts 22 can be transferred from an open position (FIG. 1) in which they are arranged at a distance from each other to a closed position (not shown), so that body tissue to be coagulated can be grasped between them.

The tool 18 is arranged at the distal end of a tube 24 of the tubular shaft 14, which comprises two sections offset parallel to each other distally and proximally, which merge into each other by double curvature of the tube 24. The tube 24 could, however, also be of straight-lined configuration or have a different kind of curvature.

The proximal section of the tube 24 is accommodated with positive locking in a bushing 26 of the tubular shaft 14. Coupling elements 28 in the form of concave recesses 28 are provided proximally on the bushing 26, and, consequently, proximally on the tubular shaft 14. The proximal section of the tube 24 defines a proximal-distal tube axis 30. The tube axis 30 can be brought into conformity with a grip axis 32 defined by the instrument grip 12 when the tubular shaft 14 and the instrument grip are connected to each other for their intended purpose. Therefore, references to the grip axis 32 hereinbelow are at the same time references to the tube axis 30 and vice versa.

Guided in the tube 24 is a pulling and/or pushing force transmission element, known per se and not shown in the drawings, which is distally in operative connection with the jaw parts 22, issues at the proximal end from the tube 24 and comprises a coupling element for coupling to the instrument grip 12.

The instrument grip 12 is configured as axial grip and comprises a substantially hollow-cylindrical, sleeve-shaped main body 34, which defines the grip axis 32. At the distal end, the instrument grip 12 has a sleeve 36 which is mounted for displacement on the main body 34 against the force of an elastic return element 35, configured as helical spring. On the inside, the sleeve 36 has coupling elements 37 in the form of latching balls 38. When the bushing 26 is inserted into the sleeve 36, the recesses 29 couple with the latching balls 38, which together form a coupling device 39 of the tubular shaft instrument, so that the bushing 26 and, consequently, the tubular shaft 14 can be releasably fixed to the instrument grip 12.

A further coupling device, which is not shown in the drawings, is formed by the coupling element, not shown in the drawings, of the pulling and/or pushing force transmission element of the tubular shaft 14. This coupling element couples with a coupling element, likewise not shown in the drawings, of the instrument grip 12 in the form of a pulling and/or pushing member, known per se, which is mounted for axial displacement in the main body 34.

For acting on the pulling and/or pushing member, the instrument grip 12 comprises two grip elements 40 and 42, which, in a manner known per se, are mounted at the proximal end of the main body 34 for pivotal movement about pivot axes extending transversely to the grip axis 32. In this context, "transversely to the grip axis 32" means in a plane aligned perpendicularly to the grip axis 32. The grip elements 40 and 42 are diametrically opposed in relation to the grip axis 32 and are of approximately half-shell-shaped configuration. From a spread position (FIGS. 1, 2 and 8) the grip elements 40 and 42 can be pivoted relative to the main body 34 and in relation thereto transferred to a close-up position (not shown). The grip elements 40 and 42 then act in a manner known per se on the pulling and/or pushing member, so that the jaw parts 22 can be acted on by means of the pulling and/or pushing force transmission element in order to actuate these.

At the proximal end, the instrument grip 12 comprises a closure element 44 which, for partial closure of the main body 34, is inserted from the proximal direction into the main body 34. In this case, the closure element 44 is of plug-shaped configuration, however, it could also be of cap-shaped or stopper-shaped configuration. An axial through-channel 46 is formed in the closure element 44. This makes it possible to connect a pipe for cleaning or flushing liquid from the proximal direction to the closure element 44 and, after use and release of the tubular shaft 14, to clean the reusable instrument grip 12 through the closure element 44. The closure element 44 engages over proximal bearing members, not shown in the drawings, of the grip elements 40 and 42, by way of which the grip elements 40 and 42 are mounted for pivotal movement on the main body 34.

Figure 5:
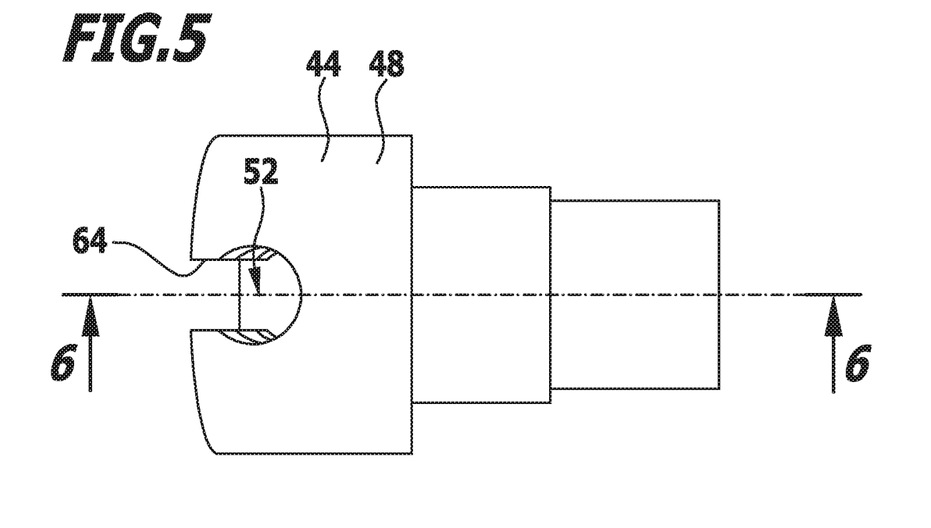
FIG. 5 shows a plan view of a closure element of the instrument grip from FIG. 1.
Figure 6:
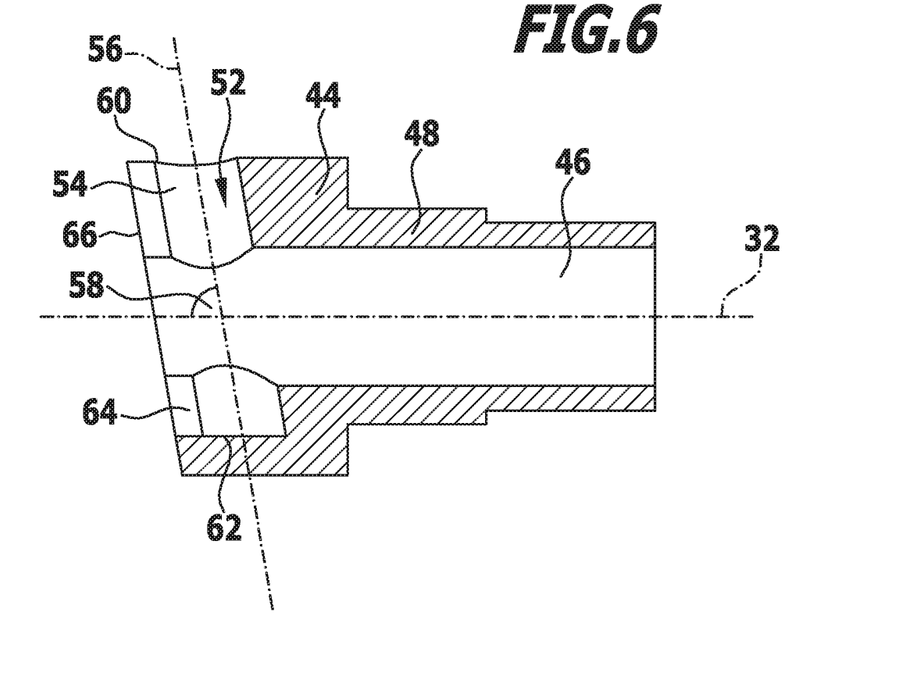
FIG. 6 shows a sectional view taken along line 6-6 in FIG. 5.

The closure element 44 is of one-piece construction and forms a connecting element 48 which can interact with a correspondingly constructed connecting element of the tubular shaft 14, details of which will be given hereinbelow, to form a connecting device 50 of the tubular shaft instrument 10. For this purpose, the closure element 44 comprises at the proximal end a receptacle 52 which is configured as blind hole 54. The blind hole 54 is formed so as to extend in a straight line in the closure element 44 and defines a hole axis 56 which includes an angle 58 with the grip axis 32. The angle 58 is an oblique angle, in relation to a proximal-distal direction, an insertion opening 60 of the blind hole 54 being arranged more proximally on the instrument grip 12 than an end of the blind hole 54 located opposite the insertion opening 60 and closed by a bottom 62 (FIGS. 5 and 6). The insertion opening 60 is arranged on the outer circumference of the closure element. The through-channel 46 and the receptacle 52 also intersect each other at the angle 58.

The closure element 44 is provided at the proximal end with a slit-shaped through-opening 64 which is formed in the proximal wall of the receptacle 52. Transversely to a plane defined by the grip axis 32 and the hole axis 56, the through-opening 64 is narrower than the blind hole 54 of round cross section. Excluded from this is the section of the receptacle 52 through which the axial through-channel 46 extends.

At the proximal end face, the closure element 44 is of planar configuration and has an abutment member 66 inclined relative to the grip axis 32. A plane defined by the abutment member 66 extends parallel to the hole axis 46 and intersects the grip axis 32 also at the angle 58.

As mentioned hereinabove, the tubular shaft 14 is a bipolar tubular shaft. The tubular shaft 14 has two electric connection lines 68 and 70 for making electrical contact. Each of the connection lines 68 and 70 is electrically connected to one of the jaw parts 22, so that these can be provided with opposite electric polarity in order to coagulate tissue grasped between the jaw parts 22 in the closed position.

The connection lines 68 and 70 are configured as flexible, electrically insulated cable lines, which, starting from the distal end 16, extend in the tube 24 as far as the bushing 26. In this way, the connection lines 68 and 70 are kept far from the operating site, which facilitates handling of the tubular shaft instrument 10 and increases its electrical safety.

As will be apparent, in particular, from FIG. 2, the tube 24 has, in relation to the tube axis 30, a lateral outlet opening 72 in the form of a through-opening 74. The through-opening 74 is arranged distally of the coupling elements 28 on the proximal section of the tube 24, which is surrounded by the bushing 26. Formed in the bushing 26 in alignment with the through-opening 74 is a through-opening 76. In the connected state of the tubular shaft 14 and the instrument grip 12, the though-openings 74 and 76 are essentially arranged immediately distally of the instrument grip 12 on the section of the bushing 26 and the tube 24, respectively, that does not engage the sleeve 36.

The connection lines 68 and 70 are led through the though-openings 74 and 76, so that they issue from the tube 24 distally of the instrument grip 12 and with their sections arranged proximally in relation to the though-openings 74 and 76 extend outside of the instrument grip 12. This allows electrical contact to be made with the tubular shaft 14 without electrical contact members having to be provided for this purpose in the instrument grip 12, differently than in the case of generic instrument grips. Constructionally simpler configurations can thus be imparted to the instrument grip 12, and, consequently, also to the tubular shaft instrument 10. The cleaning of the instrument grip 12 is also facilitated by avoiding electrical contact members, in particular, in the space surrounded by the main body 34.

Likewise, there is no need for electrical contact members to be provided on the section of the tubular shaft 14 engaging the instrument grip 12.

The sections of the connection lines 68 and 70 which have issued from the tube 24 have a common sheath 78 surrounding them. The sheath 78 is elongate and, in particular, straight-lined, for example, in the manner of a cable channel. The sheath 78 combines both connection lines 68 and 70 with positive locking for their protection and for simplified handling of the tubular shaft 14. For further protection of the connection lines 68 and 70, the sheath 78 is constructed so as to be resistant to bending. A flexible, pliable configuration of the sheath is, however, also conceivable.

The sheath 78 extends approximately from the distal end of the instrument grip 12 to its proximal end, approximately to the edge of the insertion opening 60 of the closure element 44. Transversely to the grip axis 32, the sheath 78 is arranged between the grip elements 40 and 42. Consequently, the connection lines 68 and 70 extend parallel to the grip axis 32, with the sheath 78 contacting the closure element 44 at the proximal end and otherwise extending at a short distance from the main body 34 and the sleeve 36.

The sheath 78 is positioned in such a way between the grip elements 40 and 42 that also in their position close-up to the main body 34, for actuating the jaw parts 22, the grip elements do not contact the sheath 78, and so the user does not find the sheath annoying when handling the instrument grip 12. In addition, this enables a compact design of the tubular shaft instrument 10 also in the case of the connection lines 68 and 70 extending outside of the instrument grip 12.

Figure 3:
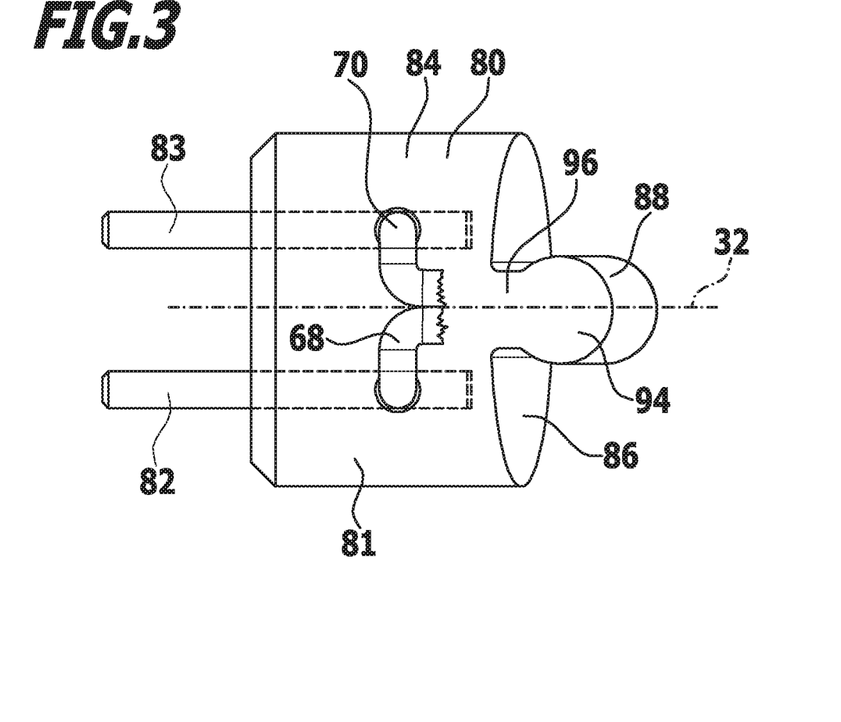
FIG. 3 shows a plan view of a connection element of the tubular shaft from FIG. 1.
Figure 4:
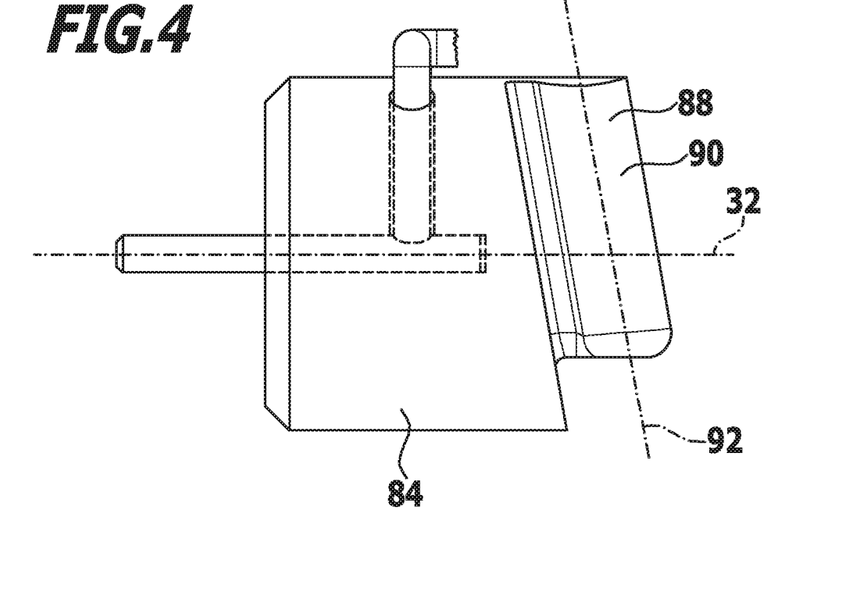
FIG. 4 shows a side view of the connection element from FIG. 3.

At the proximal end, the tubular shaft 14 has a connection element 80 arranged at the connection lines 68 and 70. The connection element 80 with a disk-shaped body 81 is of plug-shaped configuration with two electrical contact members 82 and 83, which at the proximal end face issue from the body 81 parallel to the grip axis 32 and otherwise are accommodated in the body 81. For example, the contact members 82 and 83 are molded in the body 81. In the connection element 80, one of the contact members 82 and 83, in each case, is electrically connected to one of the connection lines 68 and 70. To enable this, the proximal ends of the connection lines 68 and 70 issuing from the sheath 78 are led transversely to the grip axis 32 into the body 81, which, for this purpose, has bores for receiving the connection lines 68 and 70.

The tubular shaft 14 can be connected by means of the connection element 80 to an energy supply for providing electrosurgical energy, which can be supplied by way of the contact members 82 and 83 and the connection lines 68 and 70 to the jaw parts 22.

The, apart from the contact members 82 and 83, one-piece connection element 80 forms a connecting element 84 of the aforementioned connecting device 50. In this way, the connection element 80 can be releasably connected by positive and force locking to the closure element 44, in order to fix the proximal sections of the connection lines 68 and 70 which have issued from the tube 24 to the instrument grip 12 in a manner which is easy to handle. The connecting of the connection element 80 to and the releasing of the connection element 80 from the closure element 44 is, in particular, possible in a user-friendly manner without a tool.

The connection element 80 comprises for abutment on the closure element 44 an abutment member 86, which is of planar configuration and is arranged at the distal end face of the connection element 80. The abutment member 86 defines an inclined plane relative to the grip axis 32. The inclined plane is aligned parallel to the hole axis 56 and coincides with the plane defined by the abutment member 66 (FIG. 7). In the state in which they are connected to each other, the closure element 44 and the connection element 80 can abut on each other in flange-like manner by way of the abutment members 66 and 86 and thereby assume a specially defined relative orientation to each other.

Protruding from the abutment member 86 in the distal direction is a projection 88 of the connection element 80, which is configured as rib 90. The projection 88 defines a projection axis 92, which is inclined relative to the grip axis 32 and is aligned parallel to the plane defined by the abutment member 86.

The rib 90 is adapted in dimension and shape to the receptacle 52 and has a head section 94 positionable in the blind hole 54. The head section 94 is of round cross section and is connected to the abutment member 86 by way of a neck section 96 of the projection 88, which is narrower than the head section 94 transversely to the grip axis 32.

To connect the connection element 80 to the closure element 44, the projection 88 can be inserted into the receptacle 52 (FIG. 7), with the head section 94 engaging the blind hole 54 and the neck section 96 engaging the through-opening 64. In this way, a positive and force locking is created between the closure element 44 and the connection element 80 for reliable connection, with the axial relative positioning also being ensured by the abutment members 66 and 86 contacting each other. The projection 88 and the receptacle 52 secure the connection element 80 and the closure element 44 on each other in all three spatial directions axially along the grip axis 32 and transversely thereto.

Owing to the inclination of the coinciding hole axis 56 and projection axis 92 relative to the grip axis 32 an undercut is formed between the closure element 44 and the connection element 80 in addition to the positive locking of the projection 88 and the receptacle 52. In this way, the closure element 44 and the connection element 80 are reliably secured against unintentional release.

The connection lines 68 and 70 are of such dimensions that their sections which have issued from the tube 24 are free of axial pulling and/or pushing forces when the closure element 44 and the connection element 80 are connected to each other. In particular, the connection lines 68 and 70 are thereby relieved of strain and so damage thereto can be largely avoided.

It proves advantageous for the sheath 78 to extend distally not quite as far as the outlet opening 72 so that the connection lines 68 and 70 can be bent or folded in the area of the outlet opening 72. This makes it easier for a user to connect the connection element 80 to and release the connection element 80 from the closure element 44.

The closure element 44 at its section arranged outside of the main body 34 and the connection element 80 are of cylindrical configuration in relation to the grip axis 32 and are adapted to each other with respect to their diameter and their outer contour. In this way, the connection element 80 and the connecting element 48 are in alignment with each other, so that the connection element 80 can be regarded as proximal extension of the instrument grip 12. On the one hand, this imparts a pleasing appearance to the tubular shaft instrument 10 and, on the other hand, facilitates its handling.

The releasable connection of the closure element 44 and the connection element 80 to each other proves advantageous because the instrument grip 12 is reusable and with a plurality of tubular shafts can form an exchangeable shaft system. After use, the connection element 80 of the tubular shaft to be disposed of can be released from the instrument grip 12 and, in addition, the tube 24 can be separated from the instrument grip 12. A further tubular shaft can be connected to the instrument grip 12, and its respective connection element 80 is likewise releasably connectable to the closure element 44.

Figure 9:
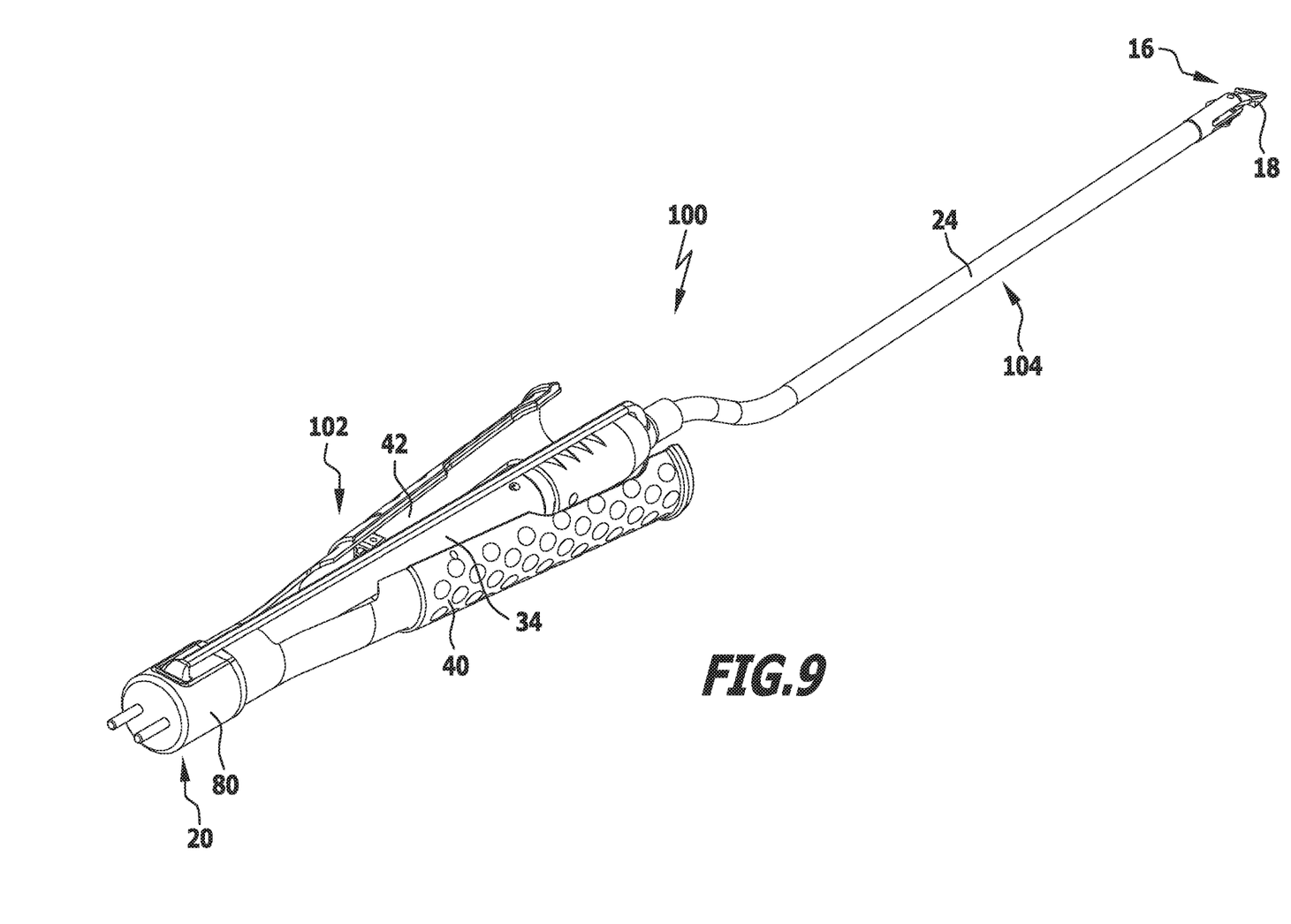
FIG. 9 shows a perspective view of a further preferred embodiment of a tubular shaft instrument in accordance with the invention, comprising a preferred embodiment of a tubular shaft in accordance with the invention and a preferred embodiment of an instrument grip in accordance with the invention, wherein the tubular shaft and the instrument grip are shown in a state in which they are connected to each other.
Figure 10:
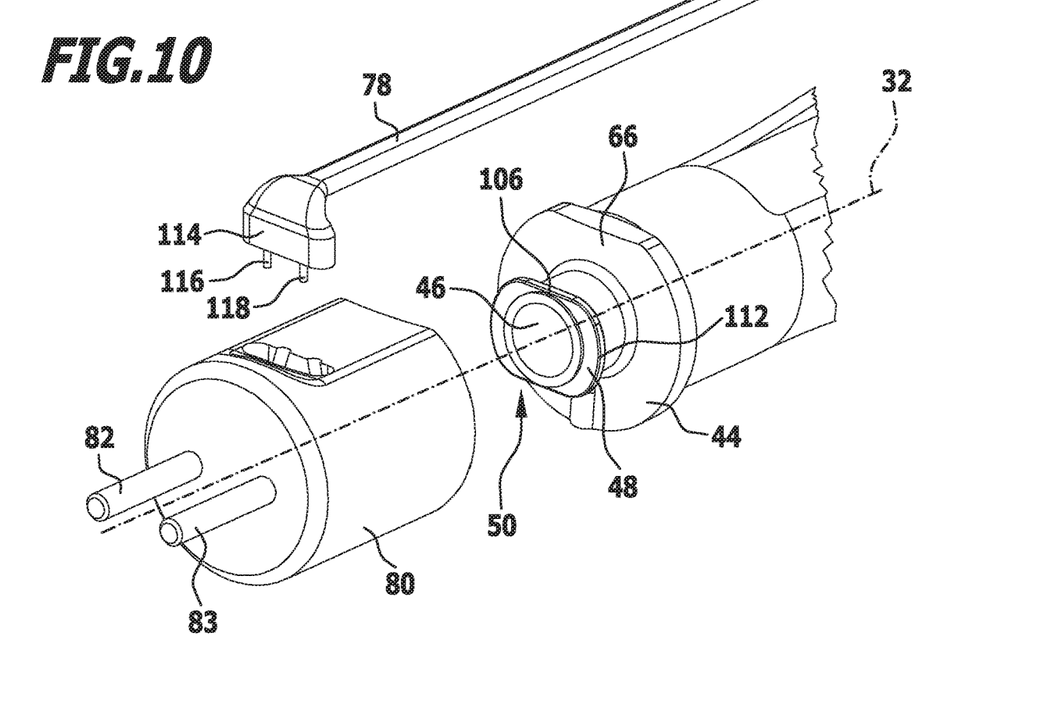
FIG. 10 shows an enlarged representation of a proximal section of the tubular shaft instrument from FIG. 9 in an exploded view.
Figure 11:
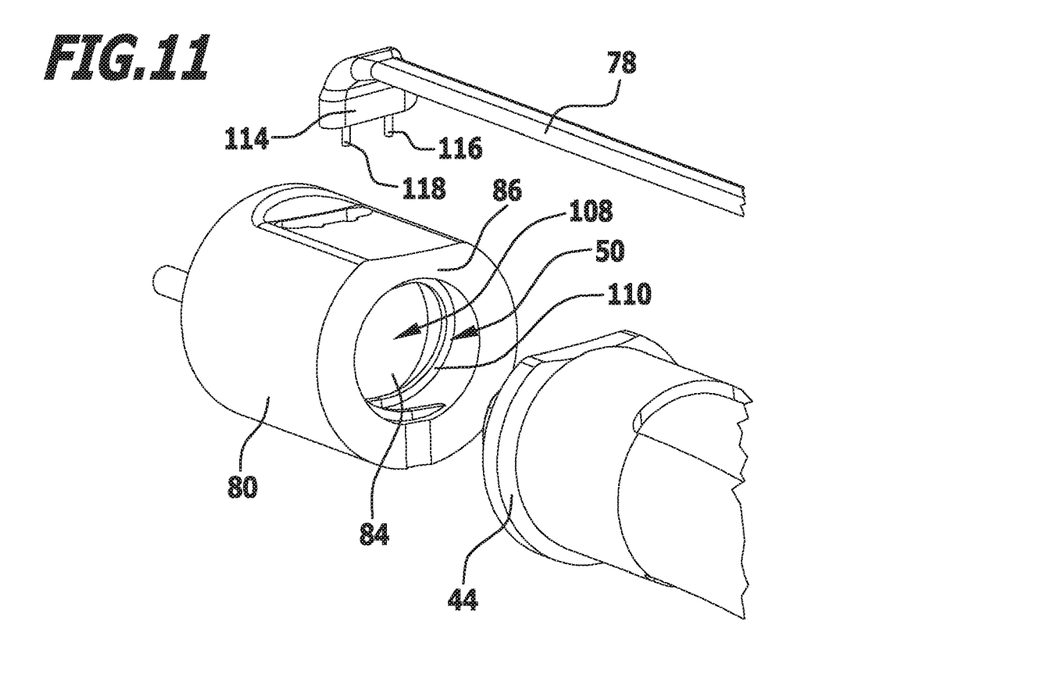
FIG. 11 shows the proximal section from FIG. 10 again from a different perspective.

FIGS. 9 to 11 show fully or partly a further advantageous embodiment of a tubular shaft instrument in accordance with the invention, denoted in its entirety by reference numeral 100. The tubular shaft instrument 100 comprises advantageous embodiments of an instrument grip in accordance with the invention and a tubular shaft in accordance with the invention, which are denoted by reference numerals 102 and 104, respectively.

The same reference numerals are used for features and components of the tubular shaft instruments 10 and 100, which are the same or have the same effect. The advantages achievable with the tubular shaft instrument 10 (and with the instrument grip 12 and the tubular shaft 14) can also be achieved with the tubular shaft instrument 100 (and accordingly with the instrument grip 102 and the tubular shaft 104). Reference is made in this connection to the explanations given hereinabove. Only the most important differences will be discussed hereinbelow.

The most important difference between the tubular shaft instruments 10 and 100 resides in the configuration of the connecting device 50, by means of which the connection element 80 is releasably fixable to the instrument grip 102. In the case of the instrument grip 102, the connecting element 48 formed by the closure element 44 is configured as projection 106 in the direction of the connection element 80. The projection 106 is aligned coaxially with the grip axis 32 and forms part of the through-channel 46.

In this case, the projection 106 is a Luer connector for connecting a flushing pipe, in particular, the projection 106 is configured for formation of a Luer lock connection. A flushing pipe can be connected to the instrument grip 102 from the proximal direction in order to clean the instrument grip 102 after use and release of the connection element 80.

In the connection element 80, the connecting element 84 is a receptacle 108. The receptacle 108 is an axially extending blind hole into which the projection 106 can be inserted. For connection to the projection 106, the receptacle 108 is of complementary configuration thereto. In particular, a Luer lock connection of the connection element 80 to the closure element 44 can thereby be made. For this purpose, the connection element 80 can be brought up close to the closure element 44 and connected to it by screwing while rotating about the grip axis 32. A thread 110 on the wall of the receptacle 108 can interact with an extension 112 of the projection 106, which is aligned transversely to the grip axis 32.

In the case of the tubular shaft instrument 100, it is also possible to connect the connection element 80 to the instrument grip 102 or to release the connection element 80 from the instrument grip 102 without a tool.

The sheath 78 of the connection lines 68, 70, not shown in FIGS. 9 to 11, is flexible in the case of the tubular shaft 104. For example, it is a flexible hose line.

Arranged at the proximal end on the connection lines 68, 70 is a plug-in member 114 with contact members 116, 118. By connecting the plug-in member 114 to the connection element 80, the contact members 116, 118 can be electrically connected to the contact members 82 and 83, respectively, and, therefore, as a result, the connection lines 68, 70 electrically contacted. The plug-in member 114 can be released from the connection element 80.

It is, of course, conceivable for the connection lines 68, 70 to be led at the proximal end into the connection element 80, as is the case in the tubular shaft instrument 10, without a releasable connection being provided therefor by way of the plug-in member 114.

What is claimed is:

1. An electrosurgical tubular shaft for use with a surgical instrument grip for formation of an electrosurgical tubular shaft instrument, comprising:
    a tube,
    an electrosurgical tool arranged at a distal end of the tube,
    at least one electric connection line electrically connected to the tool and extending in the tube,
    at least one coupling element arranged at a proximal end of the tube for interacting with at least one corresponding coupling element of the instrument grip for releasably coupling the instrument grip to the tubular shaft,
    the tube comprising an outlet opening which is arranged distally of the at least one coupling element and through which the at least one connection line issues from the tube, and
    an electric connection element for an electric energy supply, which is arranged at the proximal end on the at least one connection line,
    at least one contact member which extends from the connection element and is electrically connected to the at least one connection line,
    at least one connecting element for releasably fixing the at least one connection line to the instrument grip,
    the connection element comprises or forms the at least one connecting element, and
    the at least one contact member extends from a first portion of the at least one connecting element that is remote from a second portion of the at least one connecting element that engages with the instrument grip.

2. The electrosurgical tubular shaft of claim 1, wherein the at least one connection line issues at a side from the tube, transversely to a direction defined by the tube.

3. The electrosurgical tubular shaft of claim 1, wherein the outlet opening comprises a lateral through-opening which is formed in a cylinder wall of the tube and through which the at least one connection line issues from the tube.

4. The electrosurgical tubular shaft of claim 1, further comprising a bushing, receiving the tube, for insertion into a corresponding sleeve of the instrument grip, the bushing comprising at a proximal end at least one coupling element, and wherein there is formed in the bushing a through-opening through which the at least one connection line is led.

5. The electrosurgical tubular shaft of claim 1, further comprising a sheath surrounding the at least one connection line at a section of the at least one connection line which has issued from the tube, the sheath being one of resistant to bending or flexible.

6. The electrosurgical tubular shaft of claim 1, wherein the tubular shaft comprises a bipolar electrosurgical tubular shaft, the bipolar electrosurgical shaft comprising two electric connection lines having opposite polarity electrically connected to the tool.

7. The electrosurgical tubular shaft of claim 6, wherein a common connection element is provided, which is arranged at the proximal end on both connection lines.

8. The electrosurgical tubular shaft of claim 1, wherein the tool is a forceps tool.

9. The electrosurgical tubular shaft of claim 1, wherein the at least one connecting element is formed in one piece with the at least one connection element.

10. The electrosurgical tubular shaft of claim 1, wherein the at least one connecting element comprises or forms an abutment member for the instrument grip on a distal end face of the at least one connecting element.

11. An electrosurgical tubular shaft instrument, comprising:
    a surgical instrument grip and an electrosurgical tubular shaft,
    the surgical instrument grip comprising:
        at least one coupling element for interacting with at least one corresponding coupling element of the electrosurgical tubular shaft for releasably coupling the electrosurgical tubular shaft to the instrument grip, and
        at least one connecting element for releasably fixing at least one electric connection line of the electrosurgical tubular shaft to the instrument grip, wherein the instrument grip is void of any internal electrical contact members, and
    the electrosurgical tubular shaft comprising:
        a tube,
        an electrosurgical tool arranged at a distal end of the tube,
        the at least one electric connection line, which is electrically connected to the tool and extending in the tube,
        the at least one corresponding coupling element, which is arranged at a proximal end of the tube for interacting with the at least one coupling element of the instrument grip for releasably coupling the instrument grip to the tubular shaft,
        the tube comprising an outlet opening which is arranged distally of the at least one coupling element and through which the at least one connection line issues from the tube,
        an electric connection element for an electric energy supply, which is arranged at the proximal end on the at least one connection line, and
        at least one connecting element for interacting with the at least one connecting element of the instrument grip,
        at least one contact member which extends from the connection element and is electrically connected to the at least one connection line,
        the connection element of the electrosurgical tubular shaft comprises or forms the at least one connecting element of the electrosurgical tubular shaft, and
        the at least one contact member of the electrosurgical tubular shaft extends from a portion of the at least one connecting element of the electrosurgical tubular shaft that is remote from the instrument grip.

12. The electrosurgical tubular shaft instrument of claim 11, wherein a section of the at least one connection line which has issued from the tube is free of axial pulling and/or pushing forces.

13. The electrosurgical tubular shaft instrument of claim 11, wherein the section of the at least one connection line which has issued from the tube extends axially parallel from distal to proximal along the instrument grip.

14. The electrosurgical tubular shaft instrument of claim 11, wherein the section of the at least one connection line which has issued from the tube extends transversely to an axial direction of the instrument grip.

15. The electrosurgical tubular shaft instrument of claim 11, wherein the instrument grip comprises two actuatable grip elements for acting on the tool, with the section of the at least one connection line which has issued from the tube extending between the grip elements, in a direction transverse to the axial direction.

\* \* \* \* \*